(12) United States Patent
Vaillant et al.

(10) Patent No.: US 7,734,328 B2
(45) Date of Patent: Jun. 8, 2010

(54) SYSTEM AND METHOD TO ENHANCE VISUALIZATION OF AN OBJECT IN A VASCULAR VESSEL

(75) Inventors: Regis Vaillant, Villebon sur Yvette (FR); Jean Lienard, Igny (FR); Vincent Bismuth, Paris (FR)

(73) Assignee: General Electric Company, Schenectady, NY (US)

( * ) Notice: Subject to any disclaimer, the term of this patent is extended or adjusted under 35 U.S.C. 154(b) by 361 days.

(21) Appl. No.: 11/614,209

(22) Filed: Dec. 21, 2006

(65) Prior Publication Data

US 2008/0154122 A1  Jun. 26, 2008

(51) Int. Cl.
*A61B 5/05* (2006.01)
(52) U.S. Cl. .................... 600/426; 600/462; 382/131; 382/132
(58) Field of Classification Search .............. 600/426, 600/462; 382/131, 132
See application file for complete search history.

(56) References Cited

U.S. PATENT DOCUMENTS

| | | | |
|---|---|---|---|
| 5,771,895 A * | 6/1998 | Slager | 600/462 |
| 5,933,518 A * | 8/1999 | Cohen-Solal | 382/132 |
| 6,532,380 B1 | 3/2003 | Close et al. | |
| 6,574,300 B1 | 6/2003 | Florent et al. | |
| 2002/0136440 A1* | 9/2002 | Yim et al. | 382/131 |
| 2004/0096088 A1* | 5/2004 | Kohle | 382/128 |
| 2006/0155188 A1* | 7/2006 | Walczak et al. | 600/421 |

OTHER PUBLICATIONS

"StentBoost for Interventional Cardiology," Philips—Medical Systems. http://www.medical.philips.com/main/products/cardiovascular/products/stentboost/stentboost.html.

* cited by examiner

*Primary Examiner*—Eric F Winakur
*Assistant Examiner*—Ellsworth Weatherby (57) ABSTRACT

An imaging system of an object in an imaged subject is provided. The imaging system includes an image detector and a guidewire in support of a pair of markers. The imaging system also includes a controller in communication with the image detector. The controller includes a processor in communication to execute a series of programmable instructions stored in a memory, the programmable instructions including acquiring a plurality of acquired images, detecting a position of the pair of markers, calculating a first mathematical representation of an alignment of the guidewire between the markers and a second mathematical representation of an alignment of the guidewire not between the markers, and registering the first and second mathematical representations of the guidewire extending through the object relative to more than one of the acquired images so as to locate the object in at least one of the acquired images.

12 Claims, 5 Drawing Sheets

SYSTEM AND METHOD TO ENHANCE VISUALIZATION OF AN OBJECT IN A VASCULAR VESSEL

BACKGROUND OF THE INVENTION

The subject matter described herein generally relates to a system and method of visualising an object travelling through a vascular vessel of an imaged subject.

Fluoroscopy-guided interventional procedures typically involve introducing a catheter equipped with specific device (e.g., stent) into a patient's vascular tree. This procedure is typically performed in conjunction with injection of a contrast agent into and acquisition X-ray images of the vessels of interest. Compared to surgery, this interventional approach can be realized without making any major cut or incision in the patient, increasing opportunities for shorter recovery times and shorter hospital stays.

One example of a fluoroscopy-guided interventional procedure is an angioplasty procedure that includes delivery of a stent to a vascular vessel of a patient. However, correct deployment of the stent into the vessel typically is known to be difficult to check because of drawbacks in the visualization of the stent in the vascular vessel of the patient. More specifically, the deployed stent has a low contrast to noise ratio and may be moving fast, for example for a coronary artery. The low contrast to noise ratio and motion increases difficulty in visualizing details and can even introduce blurring of the stent image. Visualizing the stent is also known to be difficult when deployed nearby an existing stent.

BRIEF DESCRIPTION OF THE INVENTION

There is a need for an enhanced system and method of visualising an object travelling through a vascular vessel of an imaged subject. In particular, the system and method should increase visibility (e.g. contrast to noise ratio) of the markers and of the object in the vascular vessel. There is also a need for a system and method operable to enhance visualization of existing objects or structures located internally in a vascular vessel of an imaged subject (e.g. a deployed stent). The subject matter described herein addresses the needs and drawbacks described above.

In one embodiment, a method of visualizing an object deployed in an imaged subject is provided. A guidewire extends through the object, the guidewire in support of a pair of markers. The method includes acquiring a series of acquired images, each image including an illustration of the pair of markers; detecting a position of the pair of markers; calculating a first mathematical representation of an alignment of the guidewire between the markers and a second mathematical representation of an alignment of the guidewire not between the markers; and registering the first and second mathematical representation of the guidewire extending through the object in more than one of the series of images so as to locate the object in at least one of the series of acquired images.

In accordance with another embodiment, an imaging system of an object in an imaged subject is provided. The imaging system includes an image detector operable to generate an image of the imaged subject, and a guidewire in support of a pair of markers. The guidewire extends through the object. The imaging system also includes a controller in communication with the image detector. The controller includes a processor in communication to execute a series of programmable instructions stored in a memory, the programmable instructions including acquiring a plurality of acquired images, each image including an illustration of the pair of markers, detecting a position of the pair of markers, calculating a first mathematical representation of an alignment of the guidewire between the markers and a second mathematical representation of an alignment of the guidewire not between the markers, and registering the first and second mathematical representations of the guidewire extending through the object relative to more than one of the plurality of images so as to locate the object in at least one of the plurality of acquired images.

In accordance with yet another embodiment, a computer readable medium operable to store a plurality of computer-readable programming instructions for execution by a processor is provided. The plurality of computer readable programming instructions comprise acquiring a plurality of acquired images, each image including an illustration of a pair of spaced markers located along a guidewire extending through an object; detecting a position of the pair of spaced markers; calculating a first mathematical representation of an alignment of the guidewire between the markers and a second mathematical expression of an alignment of the guidewire not between the markers; and registering and illustrating the mathematical representation of the guidewire extending through the object in more than one of the plurality of acquired images.

BRIEF DESCRIPTION OF THE DRAWINGS

The following description illustrates examples of possible implementation of the invention and should not be considered as limitative. It should be read in relation with the following drawings.

DETAILED DESCRIPTION OF THE INVENTION

Figure 1:
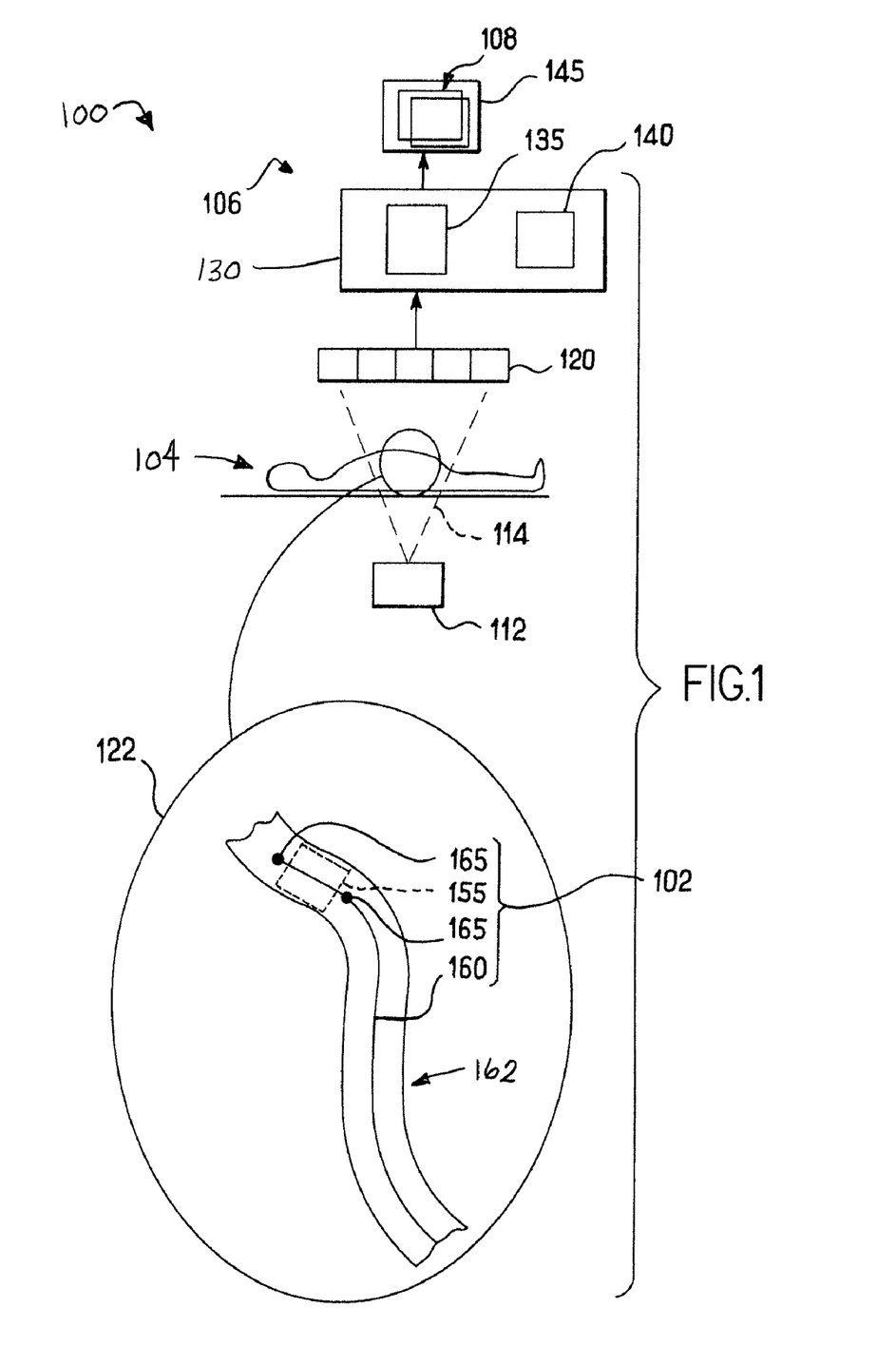
FIG. 1 is a schematic diagram illustrative of one embodiment of an imaging system operable to enhance visualization of a structure in a region of interest of an imaged subject.

FIG. 1 illustrates an embodiment of a system 100 to track travel or navigation of an image-guided object or structure 102 in an imaged subject 104. The system 100 comprises an imaging system 106 operable to acquire an image or a sequence of images 108 (e.g., x-ray image, fluoroscopic image, magnetic resonance image, real-time endoscopic image, etc.) illustrative of the deployment of the object 102 through the imaged subject 104. Thus, it should be understood that reference to the image 108 can include one or a sequence of images or image frames.

One embodiment of the imaging system 106 generally includes a radiation source 112 projecting a radiation beam 114 through the imaged subject 104 to be received at an image detector 120 in a conventional manner. The beam 114 is attenuated as it passes through imaged subject 104, until impinging upon the image detector 120, generating the image or image frames 108 illustrative of a region of interest 122 of imaged subject 104. The image detector 120 is connected to communicate the acquired image or sequence of images to a controller 130 (130 is not in the drawings).

The image or sequence of image frames 108 is digitized and communicated to a computer-readable memory 135 of the controller 130. The controller 130 further includes a processor 140 operable to execute the programmable instructions stored in the memory 135 of the system 100. The programmable instructions are generally configured to instruct the processor 140 to process the sequence of acquired images or image frames 106 so as to generate an enhanced image or sequence of images 108 for illustration on a display 145. One embodiment of the memory 135 includes a hard-drive of a computer integrated with the system 100. The memory 135 can also include a computer readable storage medium such as a floppy disk, CD, DVD, etc. or combination thereof known in the art.

One embodiment of the image-guided object or structure 102 includes a stent 155 in combination with a guidewire 160 to deploy the stent 155 in a desired position in a vascular vessel 162 of the patient 104. Markers (e.g., opaque marker balls, etc.) 165 and 166 are located at the ends of, and accordingly generally define the limits of, the stent 155. An embodiment of the markers 165, 166 are of greater diameter or thickness relative to the diameter of the guidewire 160 so as to be more readily identifiable in the acquired images 108. The limits of the guidewire 160 in both directions generally extend through and beyond the limits of the stent 155 as defined by the markers 165. The markers 165, 166 are generally comprised of an opaque material composition (e.g., metal) that is detectable on the acquired radiological images 106. Thereby, the markers 165 generally allow identification or location of the stent 155 therebetween in the acquired radiological images 106 of the imaged subject 104.

A technical effect of the system 100 is to enhance visualization of the object 102 in the image 108 by stabilizing an illustration of the object 102 in the images 108, and averaging this stabilized illustration of the object 102 to improve contrast to noise ratio in the image 108. Stabilization is achieved by generating a best fitting mathematical model, transformation, or representative of the alignment of the object 102. In a specific example, the system 100 stabilizes alignment of the stent 155 by stabilizing the guidewire 160 extending through the stent 155. Enhanced visualization of the guidewire 160 in combination with the pair of markers 165, 166 allows enhanced tracking and navigation of the stent 155. Assuming the guidewire 160 moves with the vascular vessel 162 of the patient 104, assuming that the stent 155 moves with the guidewire 160, and assuming that the distance between the stent 155 and the guidewire 160 is generally the same, the system 100 thereby allows identification and registration of the stent 155 for illustration in one or more of a sequence of acquired images 108.

Having described the general construction of the system 100 to track deployment of an image-guided object or structure 102 in an imaged subject 104, the following is a description of a method 200 of deploying the image-guided object or structure 102 through the patient 104. It should be understood that the foregoing sequence of acts comprising the method 200 can vary, that the method 200 does not need to include each every act in the following description, and the method 200 can include additional acts not disclosed in the following description. One or more of the following acts comprising the method 200 can be represented as computer-readable programmable instructions for execution by the processor 140.

Figure 2:
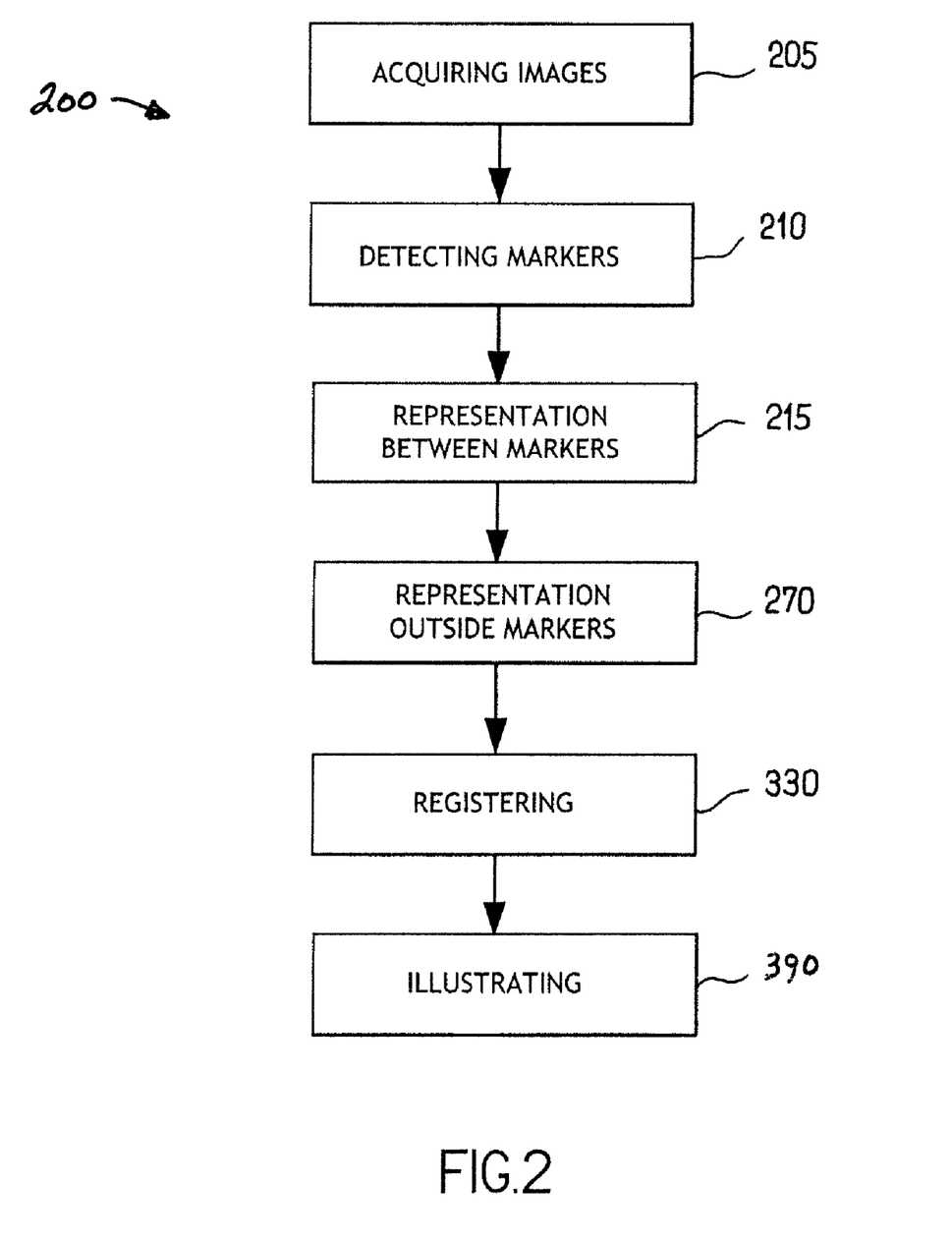
FIG. 2 is a block diagram illustrative of one embodiment of a method for enhancing the visualization an object of interest in a vessel.

Referring now to FIG. 2, act 205 of the method 200 includes acquiring a sequence of images of the region of interest of the patient where the stent 155 stands. (I erased because the stent is already deployed in most cases). Act 210 includes processing each acquired image so as to identify or detect the pair of markers 165 and 166 in the region of interest (ROI) of the imaged subject 104. Once the markers 165 and 166 (e.g., marker balls) are located, the images may be processed in order to subtract the background outside the ROI of the imaged subject 104. In one embodiment, act 210 includes employing conventional techniques to perform an estimation and subtraction of the background from the acquired images 108, leaving only an illustration of the stent 155, the guidewire 160 and the markers 165, 166 as represented by pixels in the remaining portion of the image 108.

Act 215 includes selecting one of the sequence of images 108 so as to generate a mathematical representation of an alignment of the guidewire 160 illustrated therein. In accordance with this example of act 215, a series of criteria are set for the image 108, including that a coordinate system defined in the image of the guidewire 160 is a rectangular coordinate system (e.g., x-y coordinate system) characterized with an origin (e.g., x=0, y=0 if a two-dimensional image or x=0, y=0, z=0 if a three-dimensional image) centrally located between the positions of the markers 165 and 166, an x-axis that extends through the markers 165 and 166, a y-axis generally orthogonal to the x-axis and extending through the origin, and that a zenith of the calculated parabola is located at x=0. Yet, it should be understood that the method 200 can include additional criteria, and that the criteria can change for other types of coordinate systems (e.g., polar coordinate system) or other mathematical modelling techniques employed to characterize alignment of the guidewire 160.

Figure 3:
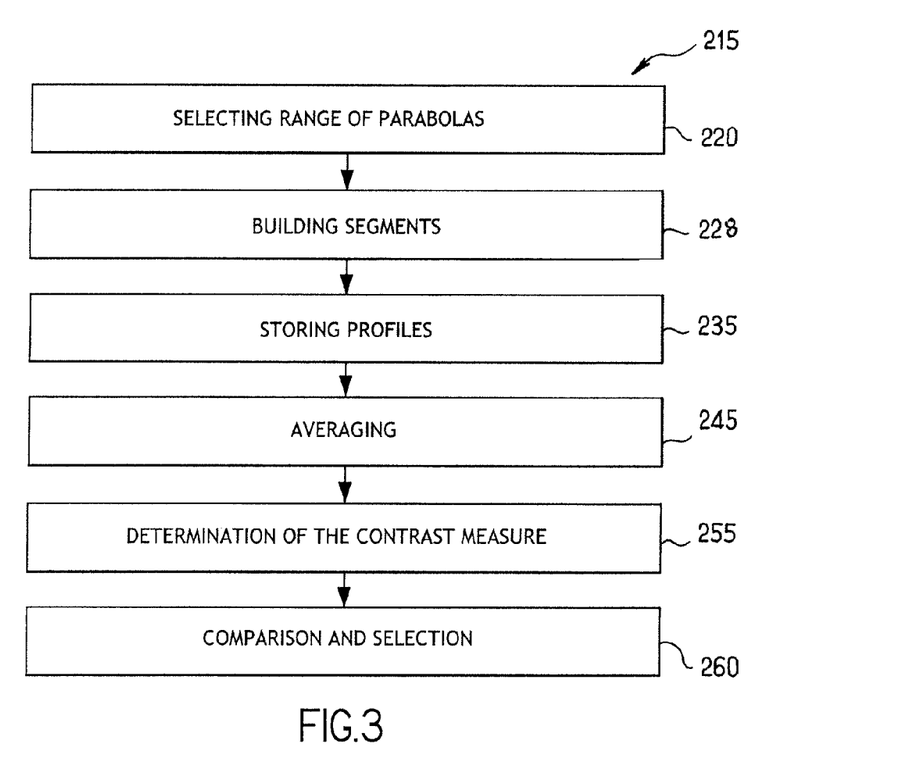
FIG. 3 is a block diagram illustrative of one embodiment of a method of calculating a parametric curve representation of a portion of the object of interest.

Referring to FIG. 3, act 220 includes selecting a range or series of candidate mathematical transformations, models, equations, or the like 222, 224, and 226 (See FIG. 4) to represent the alignment of the guidewire 160 between the markers 165 and 166 and that satisfy the criteria described above. In accordance with one embodiment of act 220 as shown in FIG. 5, the types of mathematical representations include parametric curves (e.g., parabolas) 222, 224, and 226. Yet, other types of mathematical representations, transformations, or models (e.g., string of linear models, higher order polynomial equations, etc.) can be employed to represent the alignment of the guidewire 160. The range of parabolic curves 222, 224, and 226 can be selected from a series of mathematical models of parabolas that are stored in the memory 135 of the system 100. The number and types or combinations of parabolic curves or other mathematical representations or transformations combinations thereof can vary.

Figure 5:
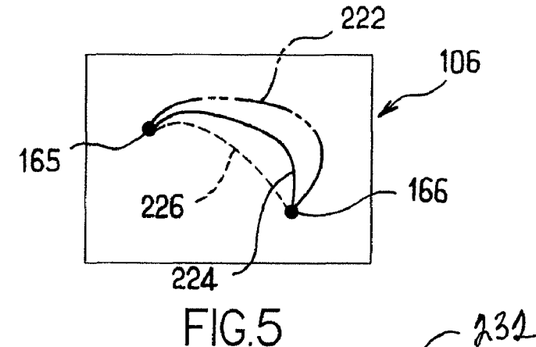
FIG. 5 is a schematic diagram illustrative of a series of candidate parametric curve representations of the object of interest between a pair of markers.
Figure 6:
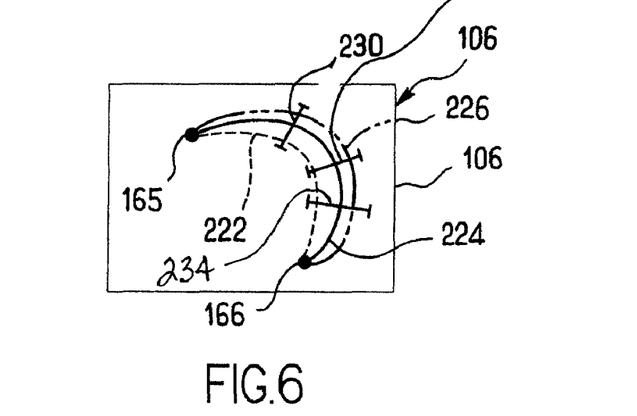
FIG. 6 is a schematic diagram illustrative of a series of cross-sections or segments along each of the candidate parametric curve representations of the object of interest between a pair of markers.

As shown in FIG. 6, act 228 includes building a series of cross-sectional segments or planes 230, 232, and 234 aligned generally perpendicular to each of the parabolic curves 222, 224, 226. FIG. 5 shows an example of the cross-sectional segments 230, 232, and 234 built along the length of, and extending through each of, parabolic curves 222, 224 and 226. Each of the cross-sectional segments 230, 232, and 234 is generally centered on and spaced from one another by a predetermined step or length along the length of each of parabolas 222, 224 and 226.

Figure 7:
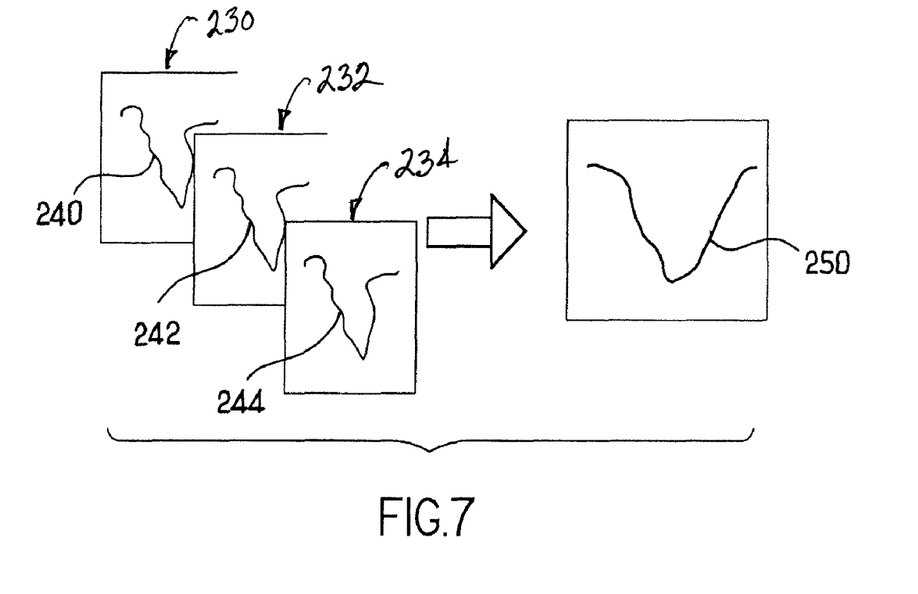
FIG. 7. is a schematic diagram illustrative of one embodiment of a method of calculating an average contrast profile.

Referring to FIG. 7, act 235 (See FIG. 3) includes detecting and storing cross-section or contrast profiles 240, 242, and 244 comprising detected greyscales values of pixels in the image 108 along each of the cross-sectional segments 230, 232, and 234, respectively for each of the series of parabolic curves 222, 224, and 226. Each cross-section or contrast profile 240, 242, and 244 thereby illustrates a contrast or difference of a grey-scale value of pixels indicative of the guidewire 160 relative to a background of the remainder of the image 108. As shown in FIG. 6, each of the contrast profiles 240, 242 and 244 comprises a measure and an illustration of grayscale values of pixels located along the respective segment line 230, 232, and 234 along each parabolic curve 222, 224, and 226 plotted or mapped relative to their detected or measured greyscale value. Pixels indicative of the guidewire 160 are expected to appear darker relative to the background. Although the illustrated profiles 240, 242 and 244 show interconnections between each data point, this is not necessary. It should be understood that the number of profiles 240, 242 and 244 can vary in accordance with the number of segments 230, 232 and 234.

Still referring to FIG. 7, act 245 (See FIG. 3) includes averaging or combining the series of generated cross-section or contrast profiles 240, 242 and 244 so as to calculate an average contrast or average profile 250 of the contrast along the series of segments 230, 232, and 234 for each of the series of parabolic curves 222, 224, 226. Although the illustrated average contrast 250 is shown for the segments 230, 232, and 234 of the parabolic curve 224, it should be understood that the average contrast for the parabolic curves 222 and 226 is calculated in a similar manner.

Act 255 includes calculating a minimum contrast or difference in measured grayscale values of pixels for the average contrast 250. In one embodiment, for each of the series of parabolic curves 220, 222 and 224, the minimum contrast of the respective average contrast 250 is compared to a predetermined threshold. One embodiment of calculating the contrast is equal to the grayscale value of the pixel at x=0 minus the averaged grayscale values at both outward extremities relative to x=0, and the resultant difference divided by the averaged value at both outward extremities. Another embodiment of calculating the contrast is equal to the grayscale value at a minimal absolute derivative (e.g., zero slope) of the average contrast 250, less the average of the grayscale values at the outward extremities of the average contrast 250. If the calculated contrast does not meet a threshold value, then selection of the respective parabolic curve 222, 224 and 226 is undesired. If all of the calculated contrasts do not meet the threshold, then the method 200 can include selecting a higher order mathematical representation or model (e.g., $3^{rd}$ order polynomial) of the alignment of the guidewire 160, or select another of the acquired images 108 of higher image quality for examination.

Act 260 includes identifying the best fitting parabolic curve 222, 224, and 226 as representative of the alignment of the guidewire 160 between the markers 165, 166. One embodiment of act 260 includes a comparison of the calculated contrast value for the average contrast 250 of each of the parabolic curves 222, 224, and 226. Tests of the above-described algorithm have demonstrated adequate accuracy and robustness to noise for a wide database of clinical image sequences.

Assume for sake of example that the parabolic curve 222 is selected as the best-fitting parametric curve for the alignment of the guidewire 160 between the markers 165, 166. Act 270 includes generating a best-fitting prolongated parabolic curve or curves for a remainder of the guidewire 160 not located between the markers 165, 166. An embodiment of act 270 includes examining the entire guidewire 160 as a series or succession of interconnected parametric curves. The succession of parametric curves can be smoothly articulated such that a point of interconnection of abutting parabolic curves is continuous and of the same general value of first derivative. Thereby, the overall mathematical transformation of the guidewire 160 is well-defined in the image 108.

Figure 4:
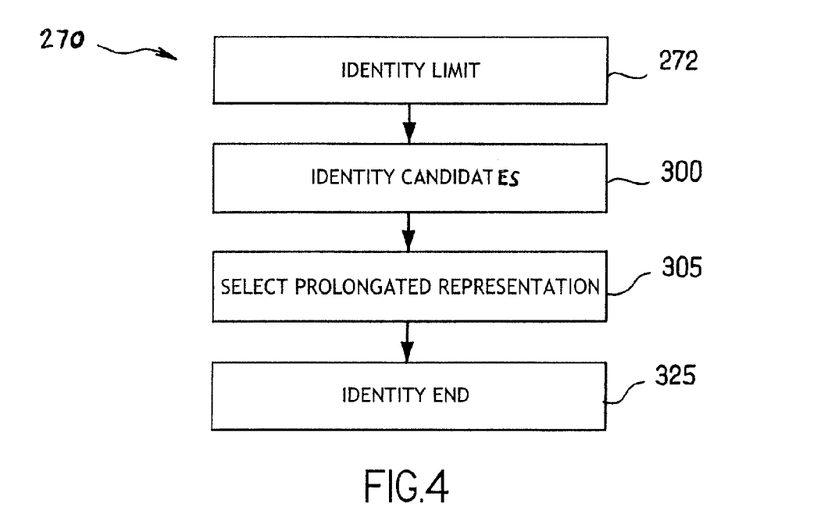
FIG. 4 is a schematic diagram illustrative of one embodiment of a method of calculating a prolongated parametric representation of a portion of the object of interest.

Referring to FIG. 4, an example of act 270 includes act 272 of identifying a designation or identifying an extremity or limit of the prior selected best fitting parabolic curve 222 are the markers 165, 166 themselves. In accordance with the illustration in FIG. 7 for sake of example, one extremity or limit of the prolongated parabolic curve 275 is set to pass through marker 166. Also, a derivative of the prolongated parabolic curve 275 is set to be generally equal to a first derivative of the selected best-fitting parabolic curve 222 between the markers 165, 166 located at the marker 166. In selecting a second extremity 280 of the prolongated parabolic curve 275, a distance 285 between the extremities 166 and 280 of the prolongated parabolic curve 275 is set or is predetermined. The distance 285 defines a circular radius within which to select or calculate the second extremity 280. Also, a rotational angle 290 of the circular radius is set or predetermined to search for the second extremity 280 of the prolongated parabolic curve 275. This rotational angle 290 is set such that the second extremity 280 is approximately located in a direction leading from the selected best-fitting parabolic curve 222 between the markers 165, 166. Still also, act 270 includes acquiring or generating a step or span between a series of candidate prolongated parabolic curves 275 for analysis.

Figure 8:
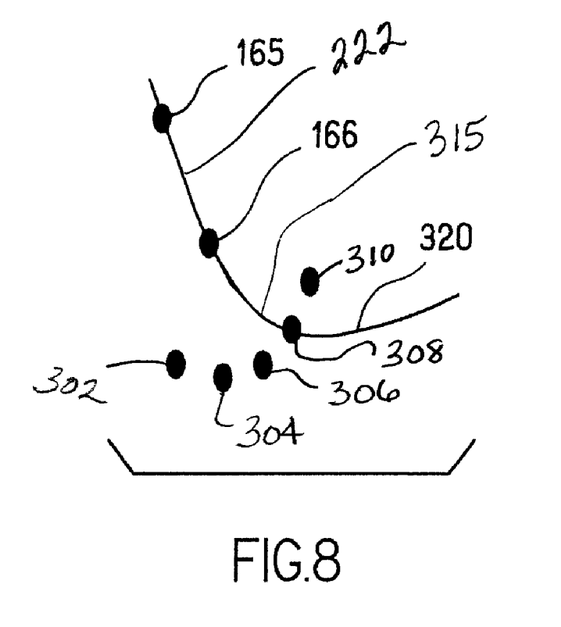
FIG. 8 is a schematic diagram illustrative of a method of calculating a prolongation of a parametric curve representation of the guidewire not between the markers.

Referring now to FIG. 8, an embodiment of act 300 includes identifying or detecting candidate pixels 302, 304, 306, 308 and 310 along the radial distance 285 and rotational angle 290 having a greyscale value indicative of the guidewire 160. For each of these candidate pixels 302, 304, 306, 308 and 310, a respective candidate parabolic curve 315 will be generated (only the candidate parabolic curve 315 through candidate pixel 308 is shown for sake of clarity) which passes through the respective candidate pixel 302, 304, 306, 308 and 310 and through the first extremity 166 of the prior selected best fitting parabola 222, and which connects smoothly (e.g., same derivative at common intersection point) with the prior selected best fitting parabolic curve 222.

Act 305 includes generating segments or cross-sections (similar to 230 in FIG. 5)) and respective profiles (similar to 240, 242 and 244 in FIG. 6) along the each candidate parabolic curve 315, generating an average profile (similar to 250 in FIG. 6), calculating a contrast for the average curve for comparison to a given detection threshold for validation, and identification of a best-fitting the candidate parabolic curves 315 as having the highest calculated value of contrast, similar to the description above to select the best-fitting of the parametric curves 222, 224, and 226 between the markers 165, 166 and as shown in FIGS. 4, 5 and 6. Once the best fitting prolongated parabolic curve 315 is found, the above-described process can be repeated to calculate additional prolongated mathematical representations 320 until prolongated for the entire length of the guide wire 160. It should be understood that the number of prolongated parabolic curves 320 can vary.

Act 325 includes identifying a stop or end to prolongation the representation 320 of the guidewire 160 in response to a stopping criteria. Examples of the stopping criteria include a predetermined total number of prolongations, a predetermined total length of the guidewire 160, or identification that none of the calculated contrast values of the best-fitting prolongated parabolic curves 320 is above a predetermined threshold, or combination of one or more of the above.

Act 330 includes registering the mathematical representations of the series of best-fitting parabolic curves 222 and 315 identified to represent alignment of the entire length of the guidewire 160. Act 330 generally includes combining, stacking, or interconnecting the best-fitting parabolic curves 222 and 315 in each of the acquired images 108. In accordance to one embodiment of act 330, a series of constraints are used, including that representation of the guidewire 160 is static relative to the images 108, that the parabolic curve representations 222 and 315 of the guidewire 160 from one image 108 to another map over one another, that the distance of any pixel to the parabolic curve representations 222 and 315 is generally unchanged, and that the series of parabolic curve representations 222 and 315 be continuous and smooth.

This embodiment of constraints allows for deformation of the stent 155 and of the guidewire 160. If one assumes that the stent 155 is static to the guide 160 at every point of time in the sequence of images 108, (i.e. that the stent is deforming itself like the guidewire), and if the mathematical transformation or representation of best fitting parametric curves 222 and 315 generally superpose the guidewire 160 and maintains the distance for every pixel in the image 108 to the guidewire 160 before and after transformation, every pixel indication of the stent 155 in the sequence of images 108 can be superposed in the acquired images.

Figure 9:
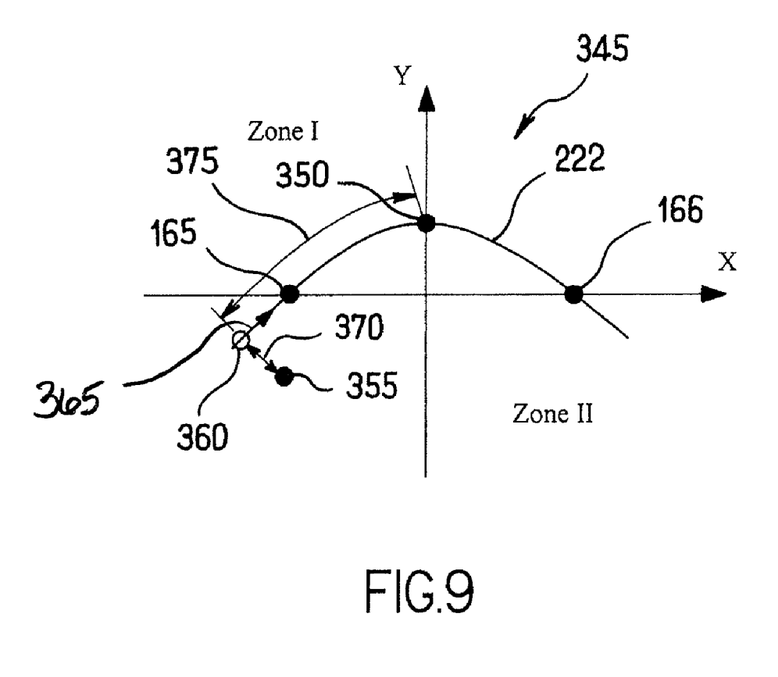
FIG. 9 is a schematic diagram illustrative of one embodiment of a method of registering the best fitting parametric curve representations for illustration on a sequence of acquired images of the imaged subject.

Referring now to FIG. 9, act 330 includes registering the mathematical representation of the parabola curve 222 of the guidewire 160 between the markers 165 and 166 with respect to the image 108.

An embodiment of act 330 includes creating a global, rigid transformation of the x-axis through the markers 165, 166 so as to cope with translation and rotation of the stent 155 (See FIG. 1) associated with navigation through the vascular vessel 162 and cardiac movement at the wall of the vascular vessel 162. A technical effect of act 330 is to make invariant an distance of a mathematical representation of the guidewire 160 relative to a common landmark of the plurality of images, and to make invariant a distance from the mathematical representation of the guidewire 160 relative to the stent 155 such that illustrations of the representations of a point of the guidewire 160 and/or the stent 155 in one image is aligned with and overlaps representations of the same point of the representations of the guidewire 160 and/or the stent 155 in another image. Accordingly, the stent 155, the guidewire 160 and the markers 165, 166 are described in a coordinate system 345 whose x-axis is defined to extend through the markers 165 and 166. The y-axis is generally orthogonal to the x-axis (at x=0) and intersects through a generally central point between the markers 165 and 166. This below-described transformation generally includes two operations: a point-to-distances operation ($T_{ptd}$), and its inverse distances-to-point operation ($T_{dtp}$).

In accordance with the operation point-to-distances ($T_{ptd}$), assume for sake of example, a normalized expression of the parabola curve 222 between the markers 165, 166 having a zenith 350 along the y-axis. For any point 355 in the domain of ($T_{ptd}$), calculate the point 360 on the parabola curve 222 that is the closest to the point 355. The segment including points 360 and 355 is generally perpendicular to the parabola curve 222 at point 360. A normalized tangential vector (illustrated by arrow and reference 365) of the parabola curve 222 is defined at point 360. A shortest distance 370 between point 355 and point 360 on the parabolic curve 160 takes the same sign (i.e., positive or negative) as a scalar product of the vector from point 355 to point 360 and the vector 365 through point 360. A second distance 375 is a length of an arc from the point 360 on the parabola curve 222 relative to the reference point 350, and takes the same sign (i.e., positive or negative) as a scalar product of as a vector from point 360 to point 350 and a vector defined from marker 165 to marker 166, resulting in a signed curvilinear abscissa along the parabola curve 222 with origin at the zenith 350 of the parabola curve 222). Accordingly, a point 355 within the ($T_{ptd}$) domain is defined by the couple or pair (370, 375) representing the distance 370 to the parabolic curve 222 and the arc length 375 defined from the projection point 360 to the reference point 350. Assume the pair (370, 375) is unique, as well as the inverse function ($T_{dtp}$) given a pair (370, 375) identifies a unique point 355 in the acquired image having a the distance 370 to the parabola curve 160 and an arc length 375 defined from the projected point 360 on the parabola curve 160 to reference point 350. Using the combination of operations for each point in the acquired image, we can perform the transformation along the guidewire 160.

The projected point 360 can be calculated by a third-degree polynomial equation. Let the parabolic curve 222 be represented as $y=ax^2+b$ in our current coordinate system 345. Values for (a) and (b) are already known. Given a point 355 represented as ($x_0$, $y_0$) in the coordinate system 345, the projected point 360 on the parabolic curve 222 that will be the closest to the given point ($x_0$, $y_0$) and such that $(x-x_0)^2+(y-y_0)^2$ is minimum and $y=ax^2+b$. This requirement can be rephrased where the equation $(x-x_0)^2+(ax^2+b-y_0)$ is a minimum. To find a value (x) that will produce a minimum, the derivative is generally equal to 0. Accordingly, a solution of the projected point 360 can be calculated as a root of the following third-degree polynomial equation:

$$x^3+px+q=0, p=(b-y_0+\tfrac{1}{2}a)/a, \text{ where } q=-x_0/2a^2.$$

The (x) searched is a real root of this polynomial.

Still referring to FIG. 9, the parabola curve 222 divides the plan or the image into zones "Zone 1" and "Zone 2". Zone I includes an area above the parabola curve 222 and zone II includes an area below the parabola curve 222. If the concavity of the parabola is opposite that shown in FIG. 9 (i.e. if the (a) parameter of the equation $y=ax^2+b$ is positive), then Zone I will be the area below the curve and Zone II the area above the curve. For a point 355 located in Zone I as shown in FIG. 9, a unique real solution can be found. For a point 355 located in Zone II, up to maximum 3 real solutions could be found (two minima and one local maxima). However, if we limit distance 370 to be less than an absolute value of a calculated radius of curvature (r) of the parabola curve 222 at point 360, then only one solution satisfies this condition. So if we define the domain of our operations ($T_{ptd}$) and ($T_{dtp}$) as a set of points whose distance 370 to the parabola curve 222 is smaller than the radius of curvature (r) at the zenith 350 of the parabola curve 222, $r_0=\tfrac{1}{2}a$, then ($T_{ptd}$) is a one-to-one map. Similarly, mapping of the domain of the inverse operation ($T_{dtp}$) is also defined as a $\tfrac{1}{2}a$ wide band around the parabola curve 222. Also, the operations ($T_{ptd}$) and ($T_{dtp}$) are continuous and differentiable. As a result, the domain of the transformation is defined as the smaller distance of the two radii. The domain of validity is a band along the guidewire 160. Numerical experiments show that for a realistic curvature of the guidewire 160, the stent 155 falls inside that band, and thus can be registered accordingly.

Based on the above-description, the guidewire 160 between the markers 165, 166 can be approximated by the parabola curve 222, and the pair (370, 375) can be calculated using the transformation operations ($T_{ptd}$) and ($T_{dtp}$). As it is assumed that the position of the stent 155 does not generally change relative to the guidewire 160, the pair (370, 375) is made an invariable quantity from frame to frame of acquired images if the markers 165, 166 are respectively aligned in every image frame. This assumption allows the act 340 of registering the parabola curve 222 as representative of the guidewire 160 in each of the acquired sequence of images 108. As a length of arc between the markers 165, 166 changes a little from image frame to image frame, a pair (370, 375) comprising the distance 370 and a normalized distance (equal to length 375 divided by an arc length of the parabola curve 222 between markers 165, 166) is defined to be invariable.

Act 330 also includes registering the remainder of parabola curve representations selected to represent alignment of the guidewire 160.

In a similar manner, we assume maintaining a distance from a point on the stent 155 to the guidewire 160 before and after the transformation, and to find a pair (370, 375) relative to the remaining selected parabola curve representations that are invariable from image frame to image frame. It is assumed that a first order derivative is continuous at junctions between differing parabola curves so to reduce ambiguity in the parabolic representation of the guidewire 160.

This simple generalization can be shown to be continuous in one to one mapping from one image frame 108 to another in a given or predetermined radius from the guidewire 160.

Act 390 includes illustrating each of the best-fitting first and second mathematical representations (e.g., parabolic curves 222 and 315) and any additional parabolic curve representations identified to represent alignment of the entire length of the guidewire 160 in the display 145.

As will be understood, the above-described mathematical representations or transformations are not specific to the types of parametric curve representations 222 and 315 for the guidewire 160 as described above. Various types and combinations of mathematical representations for the alignment of the guidewire 160 can be used.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A method of visualizing an object deployed in an imaged subject the object having a guidewire extending through, the guidewire in support of a pair of markers, the method comprising the acts of:

acquiring a plurality of x-ray images, at least one x-ray image including an acquired image data of the pair of markers;

detecting a position of the acquired image data of the pair of markers in one the acquired x-ray images;

calculating a first mathematical representation of an alignment of the guidewire between the markers and a second mathematical representation of an alignment of the guidewire dependent on an extremity of the first mathematical expression and that is not dependent on any markers, wherein the act of calculating the first and second mathematical representation of the guidewire includes:

identifying a plurality of candidate parametric curve representations in at least one of the plurality of x-ray images;

identifying a plurality of cross-section profiles in one or more of the acquired x-ray images along a plane generally perpendicular to each of the plurality of candidate parametric curve representations, each of the cross-section profiles generally created along each of the candidate parametric curve representations and spaced apart from one another by a given step;

generating a contrast profile comprising grey-scale values of pixels located along each cross-section profile in spatial relation to the respective candidate parametric curve representation;

calculating and comparing an average contrast of greyscale values for each of the candidate parametric curve representations; and identifying a best fitting candidate parametric curve representation from the plurality of candidate curve representations, the best fitting candidate parametric curve representation being the second mathematical representation of the guidewire; and illustrating the second mathematical representation of the guidewire extending through the object in a display relative to at least one of the plurality of images.

2. Method according to claim 1, wherein the second mathematical representation is continuous with the parametric curve representation between the pair of markers, and wherein the second mathematical representation includes a first derivative at the starting extremity of generally equal value to a first derivative of the parametric curve representation between the markers at the starting extremity.

3. Method according to claim 1, wherein the act of calculating the average contrast of one of the plurality of cross-section profiles includes calculating a difference of a detected grey-scale value at a center of each cross-section profile minus an average of a first and second grey-scale value at a respective first and second extremity of the respective cross-section profile, and divide the difference by the average of the first and second grey-scale values at the respective first and second extremities of the cross-section profile.

4. Method according to claim 1, wherein the average contrast is also compared to a threshold, wherein the candidate curve representation is rejected when the average contrast of the candidate curve representation is below the threshold.

5. Method according to claim 1, wherein if the plurality of images are stacked relative to one another, an act of registering makes each common point of the first or second mathematical representations of the guidewire in the plurality of images generally aligned relative to one another, the act of registering including:

creating a coordinate system for all of the plurality of images, the coordinate system including an x-axis that extends through the pair of markers, and making a distance of the first or second mathematical representations of the guidewire relative the coordinate system invariant.

6. Method according to claim 1, wherein the act calculating the second mathematical representation of the guide wire outside the pair of markers in acquiring a predetermined value of the following parameters:
- a distance between a first and a second extremity of the at least one parametric curve representation,
- an angular displacement to detect for an illustration of the guidewire in the image about the first extremity of the at least one parametric curve representation, and
- a step between each of the at least one parametric representation.

7. An imaging system of an object in an imaged subject, comprising:
- an image detector operable to acquire a plurality of x-ray images of the imaged subject;
- a guidewire in support of a pair of markers, the guidewire extending through the object; and
- a controller in communication with the image detector, the controller including a processor in communication to execute a plurality of programmable instructions stored in a memory, the programmable instructions including:
  - identifying a plurality of candidate parametric curve representations in at least one of the plurality of x-ray images;
  - identifying a plurality of cross-section profiles in one or more of the plurality of x-ray images along a plane generally perpendicular to each of the plurality of candidate parametric curve representations, each of the cross-section profiles generally created along each of the candidate parametric curve representations and spaced apart from one another by a given step;
  - generating a contrast profile comprising grey-scale values of pixels comprising the one or more x-ray images, the pixels located along each cross-section profile in spatial relation to the respective candidate parametric curve representation;
  - calculating and comparing an average contrast of greyscale values for each of the candidate parametric curve representations; and
  - identifying a best fitting candidate parametric curve representation from the plurality of candidate curve representations, the best fitting candidate parametric curve representation being the second mathematical representation of the guidewire; and
- illustrating the second mathematical representation of the guidewire extending through the object in a display relative to at least one of the plurality of images.

8. The imaging system of claim 7, wherein the second mathematical representation is continuous with the parametric curve representation between the pair of markers, and wherein the second mathematical representation includes a first derivative at the starting extremity of generally equal value to a first derivative of the parametric curve representation between the markers at the starting extremity.

9. The imaging system of claim 7, wherein the act of calculating the average contrast of one of the plurality of cross-section profiles includes calculating a difference of a detected grey-scale value at a center of each cross-section profile minus an average of a first and second grey-scale value at a respective first and second extremity of the respective cross-section profile, and divide the difference by the average of the first and second grey-scale values at the respective first and second extremities of the cross-section profile.

10. The imaging system of claim 7, wherein the average contrast is also compared to a threshold, wherein the candidate curve representation is rejected when the average contrast of the candidate curve representation is below the threshold.

11. The imaging system of claim 7, wherein if the plurality of images are stacked relative to one another, an act of registering makes each common point of the first or second mathematical representations of the guidewire in the plurality of images generally aligned relative to one another, the act of registering including:
- creating a coordinate system for all of the plurality of images, the coordinate system including an x-axis that extends through the pair of markers, and making a distance of the first or second mathematical representations of the guidewire relative the coordinate system invariant.

12. The imaging system of claim 7, wherein the act calculating the second mathematical representation of the guide wire outside the pair of markers in acquiring a predetermined value of the following parameters:
- a distance between a first and a second extremity of the at least one parametric curve representation,
- an angular displacement to detect for an illustration of the guidewire in the image about the first extremity of the at least one parametric curve representation, and
- a step between each of the at least one parametric representation.

* * * * *